(12) United States Patent
Stoll et al.

(10) Patent No.: US 10,485,574 B2
(45) Date of Patent: Nov. 26, 2019

(54) CARTILAGE TRIMMERS AND ASSOCIATED METHODS

(71) Applicant: ARTHREX, INC., Naples, FL (US)

(72) Inventors: Marc Stoll, Fort Myers, FL (US); Robert Benedict, Fort Myers, FL (US)

(73) Assignee: ARTHREX, INC., Naples, FL (US)

( * ) Notice: Subject to any disclaimer, the term of this patent is extended or adjusted under 35 U.S.C. 154(b) by 174 days.

(21) Appl. No.: 15/899,523

(22) Filed: Feb. 20, 2018

(65) Prior Publication Data

US 2018/0168678 A1 Jun. 21, 2018

Related U.S. Application Data

(63) Continuation of application No. 15/017,963, filed on Feb. 8, 2016, now Pat. No. 9,936,971.

(51) Int. Cl.
| | |
|---|---|
| *A61B 17/3213* | (2006.01) |
| *A61B 17/16* | (2006.01) |
| *A61B 17/3211* | (2006.01) |
| *A61B 17/32* | (2006.01) |
| *A61B 17/00* | (2006.01) |

(52) U.S. Cl.
CPC ...... *A61B 17/3213* (2013.01); *A61B 17/1617* (2013.01); *A61B 17/1675* (2013.01); *A61B 2017/00473* (2013.01); *A61B 2017/320052* (2013.01); *A61B 2017/32113* (2013.01)

(58) Field of Classification Search
CPC .......... A61B 17/1617; A61B 17/3213
See application file for complete search history.

(56) References Cited

U.S. PATENT DOCUMENTS

| | | | |
|---|---|---|---|
| 3,176,395 A | 4/1965 | Arner et al. | |
| 4,978,258 A | 12/1990 | Lins | |
| 5,350,383 A | 9/1994 | Schmieding et al. | |
| 6,746,451 B2 | 6/2004 | Middleton et al. | |
| 7,951,163 B2 | 5/2011 | Ek | |
| 8,591,514 B2 | 11/2013 | Sherman | |
| 8,888,781 B2 * | 11/2014 | Sterrett | A61B 1/317 606/80 |
| 9,795,395 B2 * | 10/2017 | Lizardi | A61B 17/1622 |
| 2002/0032447 A1 | 3/2002 | Weikel et al. | |
| 2004/0199166 A1 | 10/2004 | Schmieding et al. | |

(Continued)

FOREIGN PATENT DOCUMENTS

| | | |
|---|---|---|
| EP | 1785103 A1 | 5/2007 |
| EP | 2218411 A1 | 8/2010 |

(Continued)

OTHER PUBLICATIONS

International Preliminary Report on Patentability for International Application No. PCT/US2017/016349 dated Aug. 23, 2018.

(Continued)

*Primary Examiner* — Christian A Sevilla
(74) *Attorney, Agent, or Firm* — Carlson, Gaskey & Olds, P.C.

(57) ABSTRACT

A cartilage trimmer according to an exemplary aspect of the present disclosure includes, inter alia, a guide pin connected to a cutter with a blade projecting from only one side of the guide pin.

6 Claims, 7 Drawing Sheets

(56) References Cited

U.S. PATENT DOCUMENTS

| | | | |
|---|---|---|---|
| 2007/0010822 A1* | 1/2007 | Zalenski | A61B 17/1659 |
| | | | 606/79 |
| 2007/0123921 A1 | 5/2007 | Ek | |
| 2009/0171359 A1 | 7/2009 | Sterrett | |
| 2010/0057087 A1* | 3/2010 | Cha | A61B 17/1626 |
| | | | 606/80 |
| 2011/0251616 A1 | 10/2011 | Osman et al. | |

FOREIGN PATENT DOCUMENTS

| | | |
|---|---|---|
| EP | 2959850 A1 | 12/2015 |
| WO | 2008073404 A2 | 6/2008 |
| WO | 2013192080 A1 | 12/2013 |

OTHER PUBLICATIONS

International Search Report and Written Opinion for PCT Application No. PCT/US2017/016349 completd Mar. 29, 2017.

* cited by examiner

CARTILAGE TRIMMERS AND ASSOCIATED METHODS

RELATED APPLICATION(S)

This disclosure is a continuation of prior U.S. application Ser. No. 15/017,963, filed Feb. 8, 2016, the entirety of which is herein incorporated by reference.

BACKGROUND

This disclosure relates to cartilage trimmers for use during a surgical procedure. Cartilage trimmers can be used to resect or remove damaged cartilage. In one example procedure, a cartilage trimmer can remove damaged cartilage on an articular surface, and then graft material can replace the defect. The remaining, undamaged cartilage establishes a stable border for the graft material.

SUMMARY

This disclosure relates to a cartilage trimmer and associated methods. In an example, a disclosed cartilage trimmer can be assembled during surgery by inserting a guide pin into a joint space and connecting a cutter, which is deployed arthroscopically, to the guide pin. In another example, the cutter is selectively moveable relative to the guide pin and deployed via an opening adjacent an end of the guide pin. In an example, a disclosed cartilage trimmer can be used to resect cartilage in relatively narrow joint spaces. In an embodiment, the cartilage is articular cartilage.

A cartilage trimmer according to an exemplary aspect of the present disclosure includes, inter alia, a guide pin connected to a cutter with a blade projecting from only one side of the guide pin.

In a further non-limiting embodiment, an angular position of the blade is adjustable relative to the guide pin.

In a further non-limiting embodiment, the angular position of the blade is adjustable relative to a normal to a longitudinal axis of the guide pin by about 20 to about 30 degrees in a distal direction and by about 20 to about 30 degrees in a proximal direction.

In a further non-limiting embodiment, the guide pin includes a first connection portion adjacent a distal end thereof, the cutter includes a second connection portion, and the first and second connection portions are connectable.

In a further non-limiting embodiment, the first connection portion includes an opening in a side of the guide pin, and the second connection portion is received in the opening.

In a further non-limiting embodiment, the connection between the first and second connection portions is threaded.

In a further non-limiting embodiment, a bushing is received in the opening, and the bushing is moveable relative to the opening to adjust an angle of the cutter relative to the guide pin.

In a further non-limiting embodiment, the second connection portion includes a slot, and the first connection portion includes a retention pin selectively moveable into the slot.

In a further non-limiting embodiment, the first connection portion includes threads about an exterior of the guide pin, and the second connection portion comprises a threaded bushing configured to be threadably engaged with the threads of the guide pin.

In a further non-limiting embodiment, the cutter includes a socket, and the threaded bushing is received in the socket. The socket is moveable relative to the threaded bushing to adjust an angle of the cutter relative to the guide pin.

A cartilage trimmer according to another exemplary aspect of the present disclosure includes, inter alia, a guide pin and a cutter. The cutter includes a blade moveable between a retracted position within the guide pin and a deployed position projecting from the guide pin. Further, the blade has a cutting surface only on a proximal edge of the blade.

In a further non-limiting embodiment, the cutter further comprises a) a rod moveable within the guide pin, and b) the blade at a distal end.

In a further non-limiting embodiment, the guide pin includes an internal passageway and an opening adjacent a distal end thereof. Further, the blade projects through the opening when in the deployed position.

In a further non-limiting embodiment, the opening is in a side of the guide pin, and the internal passageway includes an angled wall adjacent the opening to facilitate movement of the blade between the retracted position and the deployed position.

In a further non-limiting embodiment, the blade is moveable between a folded position substantially parallel to the rod and a cutting position substantially normal to the rod. The blade can also be biased to the cutting position.

In a further non-limiting embodiment, the opening is at a distal end of the guide pin.

A method of using a cartilage trimmer according to an exemplary aspect of the present disclosure includes connecting the cutter to a guide pin in a joint space. The cutter comprises a blade projecting from only one side of the guide pin.

In a further non-limiting embodiment, a method includes resecting cartilage with the blade.

In a further non-limiting embodiment, the cartilage is articular cartilage.

In a further non-limiting embodiment, the method includes adjusting an angle of the blade relative to the guide pin while resecting cartilage.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

BRIEF DESCRIPTION OF THE DRAWINGS

The drawings can be briefly described as follows:

In FIG. 1, the cartilage trimmer is unassembled.

In FIG. 2, the cartilage trimmer is assembled.

DETAILED DESCRIPTION

This disclosure relates to a cartilage trimmer and associated methods. In an example, a disclosed cartilage trimmer can be assembled during surgery by inserting a guide pin into a joint space and connecting a cutter, which is deployed arthroscopically, to the guide pin. In another example, the cutter is selectively moveable relative to the guide pin and deployed via an opening adjacent an end of the guide pin. In an example, a disclosed cartilage trimmer can be used to resect cartilage in relatively narrow joint spaces. In an embodiment, the cartilage is articular cartilage.

Figure 1:
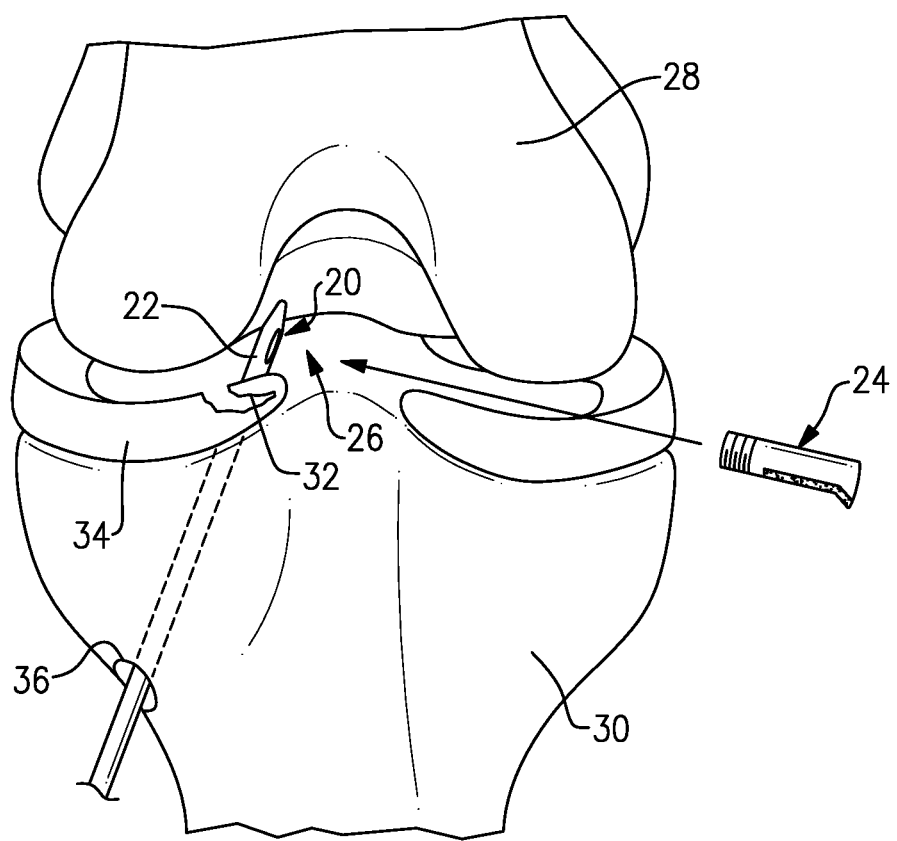
FIG. 1 illustrates a first example cartilage trimmer relative to a knee joint.
Figure 2:
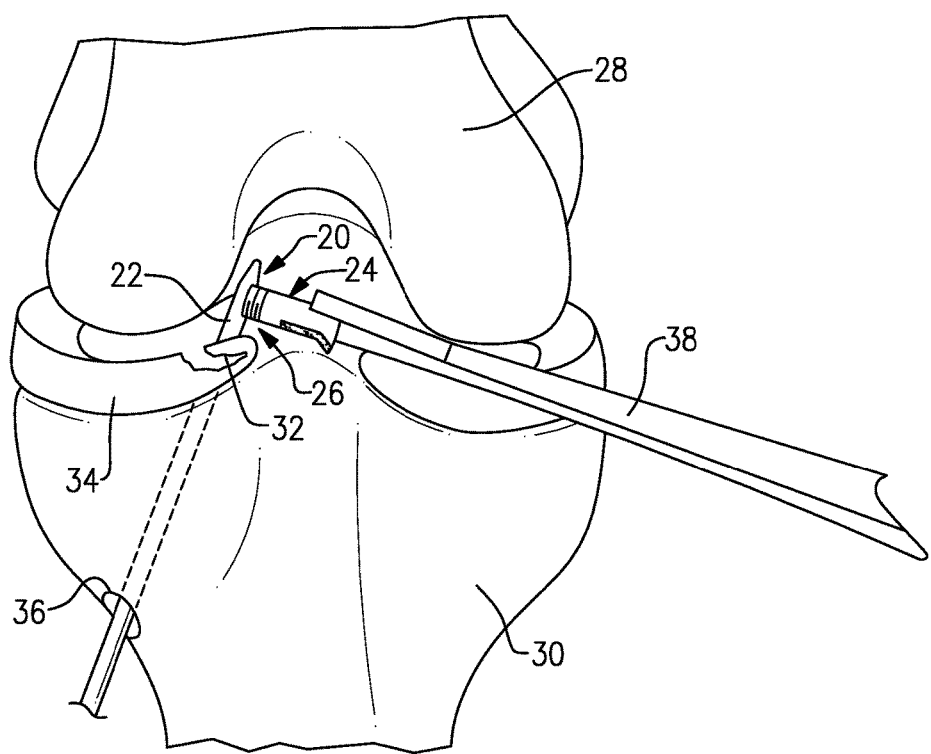
FIG. 2 illustrates the first example cartilage trimmer relative to the knee joint.

FIGS. 1-2 illustrate an example cartilage trimmer 20, which includes a guide pin 22 and a cutter 24, relative to a joint space 26. In this example, the joint space 26 is a joint cavity in a knee, and is specifically a cavity between a femur 28 and a tibia 30. While a knee joint is illustrated, this disclosure extends to cartilage trimmers for other joints.

The cartilage trimmer 20 is configured to resect torn or damaged cartilage in the joint space 26. In this example, the cartilage trimmer 20 is used to resect a tear 32 in a meniscus 34. The cartilage trimmer 20 can be used to resect other cartilage structures, including articular cartilage.

As generally mentioned above, the cartilage trimmer 20 is configured to be assembled during surgery. In the example of FIGS. 1-2, the cartilage trimmer 20 is assembled by first inserting the guide pin 22 into the joint space 26. In this example, the guide pin 22 is inserted into the joint space 26 by way of a tunnel 36 formed in the tibia 30. Once the guide pin 22 is positioned in the joint space 26, the cutter 24 is deployed arthroscopically, as generally shown in FIG. 1, and connected to the guide pin 22 by a tool 38 such as a grasper, as generally shown in FIG. 2. The assembled cartilage trimmer 20 is then used to resect the tear 32. Because cartilage is relatively soft, a surgeon typically maneuvers the guide pin 22 by hand. However, in some examples, the guide pin 22 can be rotated using an automated tool, such as a drill.

Once the tear 32 is resected, the cutter 24 can then be removed from the guide pin 22 (for example, using the tool 38). The guide pin 22 and the cutter 24 are then separately removed from the joint space 26. By assembling and disassembling the cartilage trimmer 20 during surgery, the cartilage trimmer 20 is able to reach relatively narrow joint spaces. A "narrow" joint space is a joint space, or a portion of a joint space, that is relatively small and perhaps difficult to visualize or access during surgery. Example narrow joint spaces include the lateral and medial compartments of a knee joint.

Figure 3:
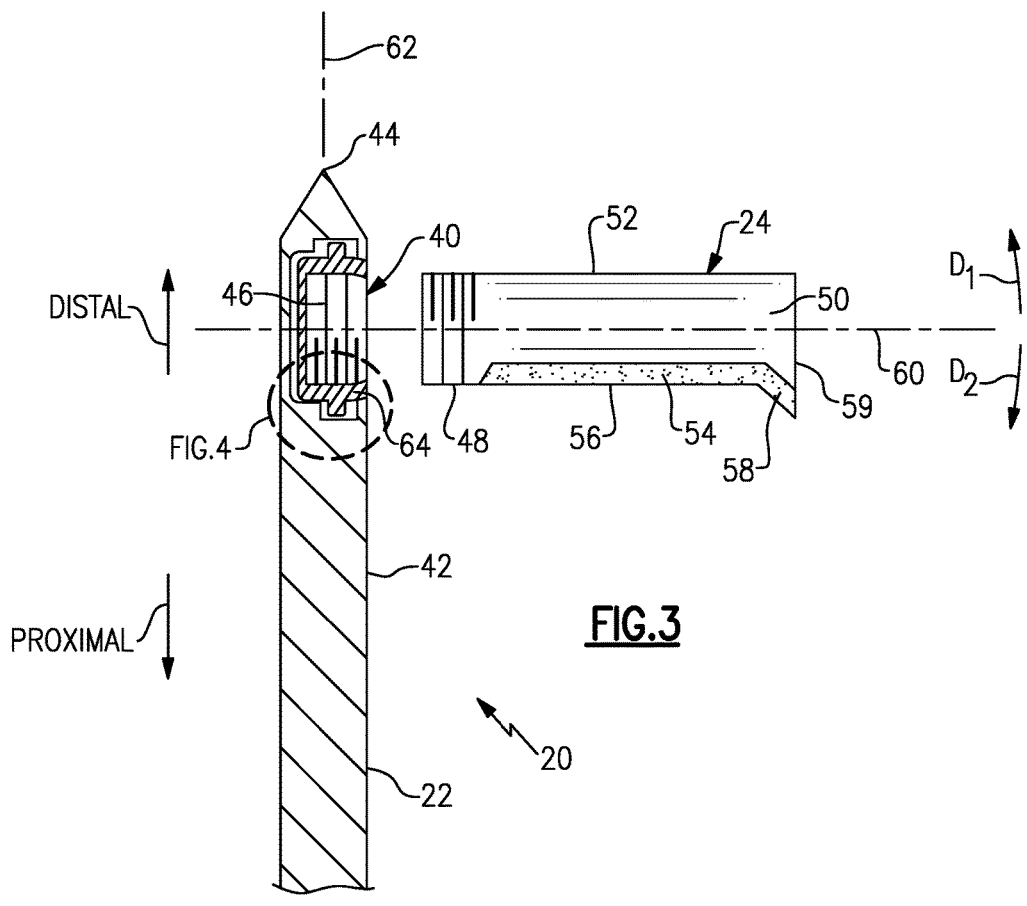
FIG. 3 is a cross-sectional view of the first example cartilage trimmer.

FIG. 3 is a cross-sectional view of the cartilage trimmer 20. In this example, the guide pin 22 includes an opening 40 on one side 42. The opening 40 is provided adjacent, yet spaced-apart from, a distal end 44 (the "distal" and "proximal" directions are labeled in the Figures) of the guide pin 22. The opening 40 includes a first connection portion 46 configured to mate with a second connection portion 48 of the cutter 24. In this example, the first and second connection portions 46, 48 are threaded and thus provide a threaded connection. Other types of connections are also within the scope of this disclosure.

The cutter 24 includes a blade 50 extending from the second connection portion 48. The blade 50 includes a blunt distal edge 52 and a cutting surface 54 providing a sharp surface at a proximal edge 56. The cutting surface 54 is configured to resect cartilage. The cutting surface 54 can optionally include a tooth 58 at a free end 59 of the blade 50 opposite the second connection portion 48.

Providing the blade 50 with a blunt distal edge 52 and a cutting surface 54 only at the proximal edge 56 decreases the risk of damage to healthy cartilage and increases the precision to resect damaged cartilage. Providing the blade 50 on only one side of the guide pin 22 also increases precision, and further allows the cartilage trimmer 20 access to relatively narrow joint spaces.

Figure 4:
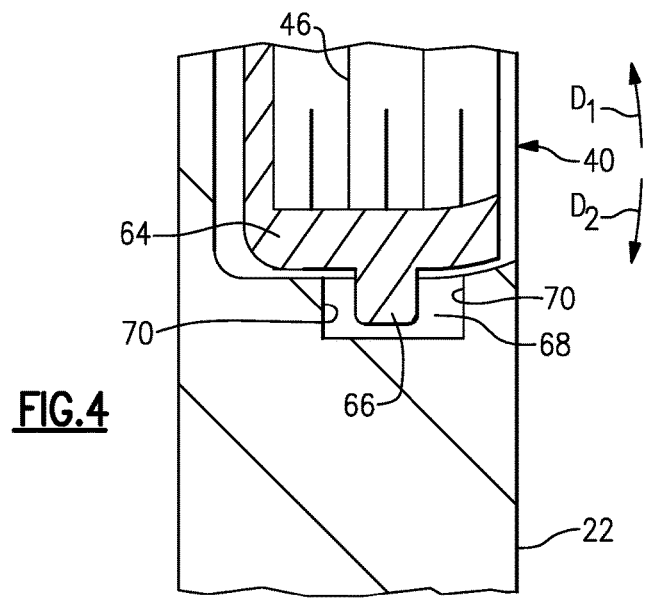
FIG. 4 is a close-up view of the encircled area in FIG. 3.

The blade 50 is configured to connect to the guide pin 22 and project along a blade axis 60, which is substantially normal to a longitudinal axis 62 of the guide pin 22. In the example of FIG. 3, an angular position of the blade 50 relative to the guide pin 22 is adjustable. In particular, the blade 50 can be inclined away from a normal to the longitudinal axis 62 in both a direction $D_1$, which is generally in the distal direction, and in a direction $D_2$, which is generally in the proximal direction. In one example, the blade 50 is adjustable away from the normal by about 20 to about 30 degrees in either of the directions $D_1$ or $D_2$. In a further example, the blade 50 is adjustable away from the normal by about 25 degrees in either of the directions $D_1$ or $D_2$. In a further example, the blade 50 is adjustable away from the normal by about 24 degrees in either of the directions $D_1$ or $D_2$. In a further example, the blade 50 is adjustable away from the normal by about 23 degrees in either of the directions $D_1$ or $D_2$. In a further example, the blade 50 is adjustable away from the normal by about 26 degrees in either of the directions $D_1$ or $D_2$. In a further example, the blade 50 is adjustable away from the normal by about 27 degrees in either of the directions $D_1$ or $D_2$. In order to facilitate the angular adjustment of the blade 50, the first connection portion 46 is provided by a bushing 64 received in the opening 40. Details of the bushing 64 are illustrated in FIG. 4. In this example, the bushing 64 includes at least one tab 66 projecting into a corresponding channel 68 in the opening 40. In the illustrated embodiment, two tabs 66 are provided on opposed sides of the bushing 64, and the opening 40 includes two channels 68 corresponding to the tabs 66.

The bushing 64 is moveable relative to the opening 40, and the movement of the bushing 64 is restricted by the arrangement of the tab 66 and the channel 68. Specifically, the bushing 64 is moveable in the directions $D_1$ and $D_2$, until the tab 66 contacts either end 70 of the channel 68. The ends 70 of the channel could be provided with resilient members, for example, configured to bias the blade 50 to a position where the blade axis 60 is normal to the longitudinal axis 62.

In an example, the angular position of the blade 50 is passively adjustable. As the cutter 24 resects cartilage, the angular position of the blade 50 is influenced by the position of the guide pin 22 relative to the adjacent cartilage. Alternatively, the guide pin 22 could incorporate a rod connected to the bushing 64 to allow for active adjustment. By allowing an angular adjustment of the blade 50, the blade 50 can be positioned at an optimal angle for resecting cartilage. The blade 50 can further be maneuvered into relatively narrow joint spaces that are not otherwise easily accessed.

Figure 5:
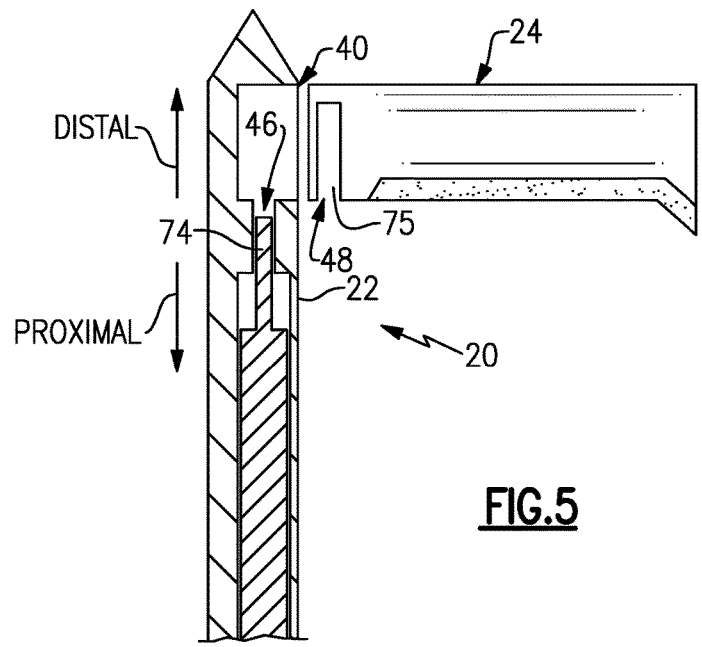
FIG. 5 is a cross-sectional view of a second example cartilage trimmer.

While the first and second connection portions 46, 48 of FIGS. 3-4 provide a threaded connection, other types of connections are also within the scope of this disclosure. For example, FIG. 5 illustrates a cartilage trimmer 20 having a slot-and-pin connection. In this example, the first connection portion 46 includes a retention pin 74 selectively moveable into the opening 40. A surgeon, for example, can selectively move the retention pin 74 relative to the remainder of the guide pin 22.

The second connection portion 48 of the cutter 24 includes a slot 75. The retention pin 74 is selectively moveable into the slot 75 to retain the cutter 24 relative to the guide pin 22. The slot-and-pin connection could allow for the angular adjustment of the blade as generally discussed above. In that case, the second connection portion 48 could include a bushing.

Figure 6:
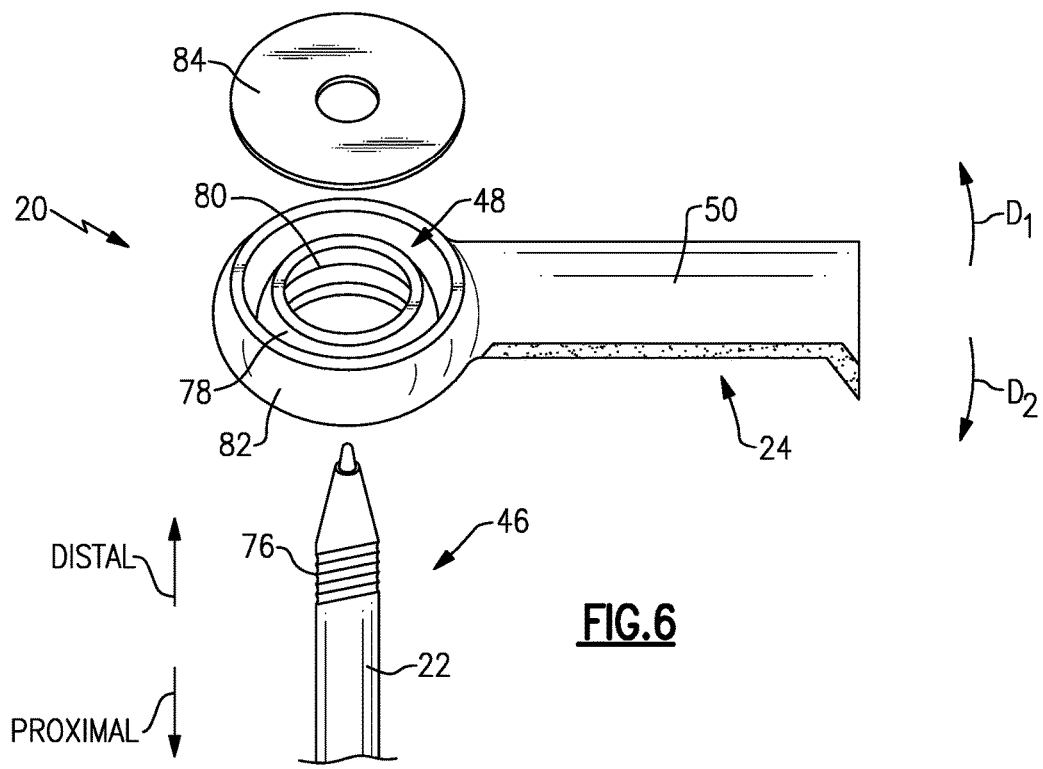
FIG. 6 is an exploded view of a third example cartilage trimmer.

FIG. 6 is an exploded view of another embodiment of the disclosed cartilage trimmer 20. In this example, the first connection portion 46 includes threads 76 provided about an exterior of the guide pin 22. The second connection portion 48 is provided by a bushing 78 having internal threads 80 and configured to be threadably engaged with the threads 76 of the first connection portion 46. The threads 76, 80 may be handed such that they do not become unwound during normal use of the cartilage trimmer 20.

In one example, the cartilage trimmer 20 can be rotated primarily in a clockwise direction from the perspective of the surgeon (i.e., when viewed from a location proximal to the cartilage trimmer 20). Such rotation may cause the threads 80 to rotate relative to the threads 76 in a counter-clockwise direction. To prevent unintended unwinding, the threads 76, 80 are handed such that the bushing 78 continues to tighten to the guide pin 22 as the surgeon rotates the cartilage trimmer 20 clockwise. In this example, the threads 76, 80 are right-handed threads. This disclosure is not limited to right-handed threads. For example, the threads 76, 78 could be left-handed threads for counter-clockwise rotation of the cartilage trimmer 20.

Figure 7:
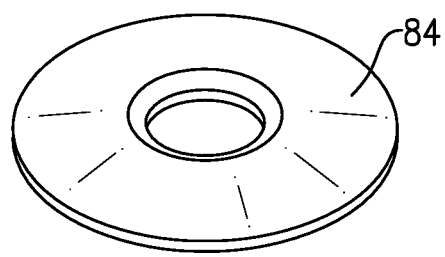
FIG. 7 is an exploded view of a bushing, socket, and plate associated with the third example cartilage trimmer.
Figure 7:
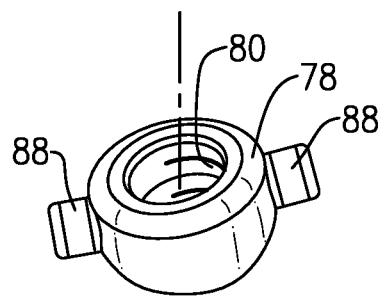
Figure 7:
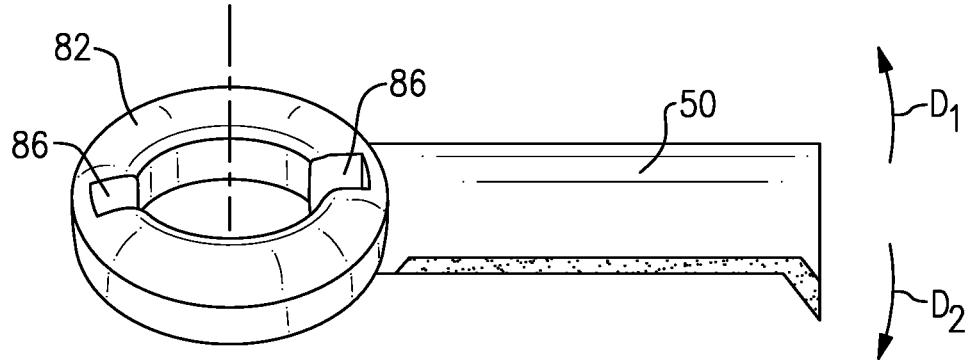

In the embodiment of FIGS. 6-7, the second connection portion 48 includes a socket 82 receiving the bushing 78. The blade 50 is rigidly connected to the socket 82 and is provided on one side of the guide pin 22. The inner surface of the socket 82 has a contour corresponding to an outer contour of the bushing 78. Thus, the socket 82 and blade 50 are moveable relative to the bushing 78 to adjust a cutting angle of the blade 50 relative to the guide pin 22.

With reference to FIG. 7, movement of the socket 82 relative to the bushing 78 is regulated in part by a plate 84 provided over the socket 82. Movement is further limited by a plurality of channels 86 formed in the socket 82. The channels 86 receive tabs 88 projecting from the bushing 78. The tabs 88 are sized to allow movement of the socket in the directions $D_1$ and $D_2$. In this example, angular adjustments of the socket 82 are passive. As the guide pin 22 moves proximally during resection, the socket 82 and the blade 50 tilt in the direction $D_1$.

Figure 8:
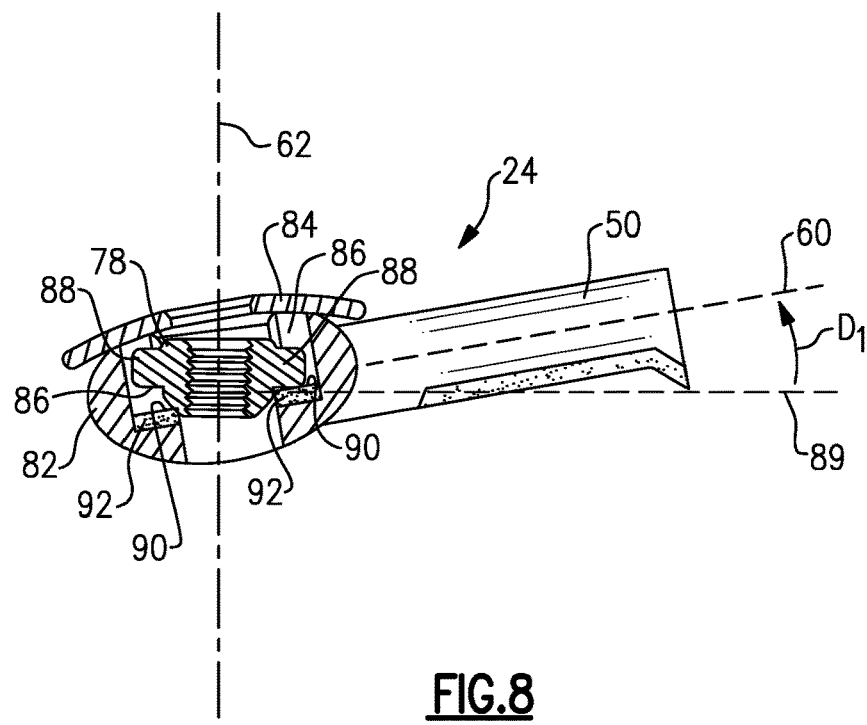
FIG. 8 is a cross-sectional view of the bushing, socket, and plate associated with the third example cartilage trimmer.

FIG. 8 shows the assembled cutter 24 in cross-section. Further, in FIG. 8, the blade 50 has been adjusted such that the blade axis 60 is transverse of a normal axis 89 and is inclined in the direction $D_1$ relative to the normal axis 89. In this example, the right-hand tab 88 is in contact with an end 90 of the channel 86. Thus, the blade 50 has moved off the normal to a limit. In this example, a resilient member 92 is provided at the end 90 of the channel to bias the blade 50 toward the normal 89. The resilient member 92 is not required in all examples. Alternatively or additionally, resilient members could be provided on the plate 84.

Figure 9:
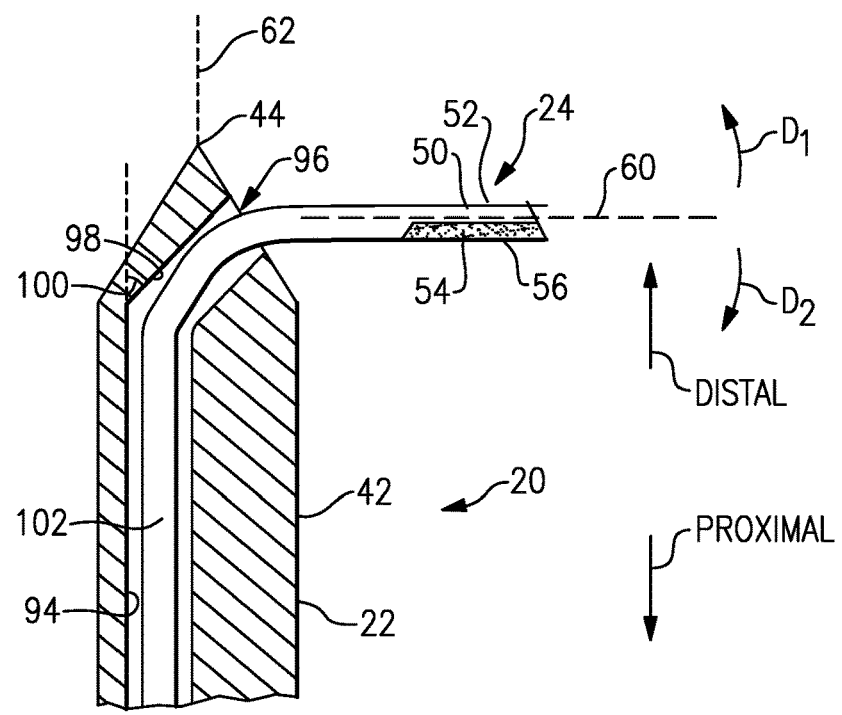
FIG. 9 is a cross-sectional view of a fourth example cartilage trimmer.
Figure 10:
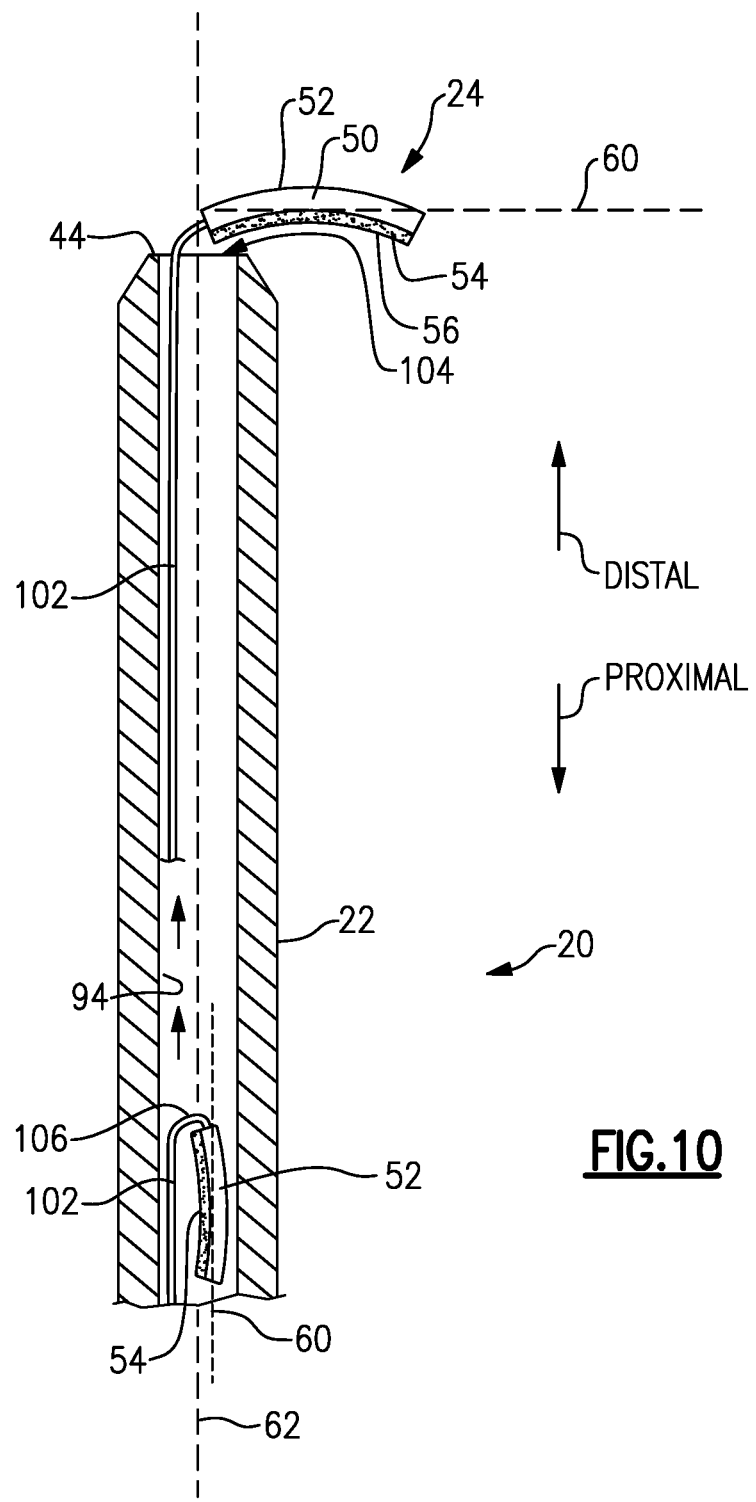
FIG. 10 is a cross-sectional view of a fifth example cartilage trimmer.

FIGS. 1-8 illustrate cartilage trimmers that are configured to be assembled during surgery. This disclosure also extends to cartilage trimmers with cutters that are selectively moveable relative to the guide pin and deployed via an opening adjacent an end of the guide pin. FIGS. 9 and 10 illustrate two such examples.

Referring to FIG. 9, the cartilage trimmer 20 includes a guide pin 22 having an internal passageway 94 extending from a proximal end to an opening 96 adjacent a distal end 44. In this example, the opening 96 is provided in a side 42 of the guide pin 22 and is spaced proximally from the distal end 44. The internal passageway 94 includes an angled wall 98 adjacent the opening 96 to facilitate movement of the blade 50 between the internal passageway 94 and the opening 96. The angled wall 98 is inclined at an acute angle 100 relative to the longitudinal axis 62 of the guide pin 22. While the angled wall 98 has a constant angle in this example, the angled wall 98 could be curved in other embodiments. Further, the angled wall 98 could include more than one wall segment.

The cutter 24 in this example includes a blade 50 connected to a distal end of a rod 102. The blade includes a blunt distal edge 52 and a cutting surface 54 at a proximal edge 56 only. The rod 102 is made of a semi-rigid material and is selectively moveable within the internal passageway 94 by a surgeon. Movement of the rod 102 translates to movement of the blade 50 between a retracted position within the internal passageway 94 and a deployed, or cutting, position projecting from the guide pin 22 via the opening 96.

The rod 102 is formed such that the blade axis 60 is biased substantially normal to the longitudinal axis 62 when the blade 50 projects through the opening 96. The material of the rod 102 allows movement of the blade 50 off of the normal in the directions $D_1$ and $D_2$. Further, the material of the rod 102 allows the blade 50 to project in a direction parallel to the internal passageway 94 when passing within the internal passageway. Example materials for the rod 102 include, but are not limited to, nitinol, PEEK, or a combination of PEEK and metal (e.g., a PEEK rod with a metal blade).

FIG. 10 shows an example cartilage trimmer 20 with a fully cannulated guide pin 22. In particular, the internal passageway 94 extends in a direction substantially parallel to the longitudinal axis 62 from a proximal end of the guide pin 22 to the distal end 44. The internal passageway 94 in this example terminates at an opening 104 at the distal end 44.

The cutter 24 in this example includes a blade 50 connected to a rod 102 by way of a hinge 106. In this example, the hinge 106 is provided by a bend in the rod 102. The hinge 106 is configured to bias the blade 50 such that the blade axis 60 is substantially normal to the longitudinal axis 62 when the blade 50 is deployed through the opening 104. The blade 50 in this example is moveable between a folded position (shown near the bottom of FIG. 10), in which the blade axis 60 is substantially parallel to the rod 102 and a cutting surface 54 is positioned adjacent the rod 102, and a cutting position (shown near the top of FIG. 10) substantially normal to the rod 102.

As with previously discussed embodiments, the distal edge 52 of the blade 50 can be blunt, which prevents damage to adjacent soft tissue as the blade 50 moves from the folded position to the cutting position. When the blade 50 is retracted back into the guide pin 22, the blade 50 would not be folded. Instead, the blade 50 would be distal of the hinge 106.

It should be understood that terms such as "proximal," "distal," "medial," and "lateral" are used consistent with their art-accepted meanings, and are used for purposes of explanation only. Terms such as "longitudinal," "axial," and "radial," are used above with reference to the respective axis and are also used only for purposes of explanation, and should not be considered otherwise limiting. Terms such as "generally," "substantially," and "about" are not intended to be boundaryless terms, and should be interpreted consistent with the way one skilled in the art would interpret those terms.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A cartilage trimmer, comprising:
a guide pin; and
a cutter including a blade moveable between a retracted position within the guide pin and a deployed position projecting from the guide pin, wherein the blade has a cutting surface only on a proximal edge of the blade,
wherein the cutter further comprises a) a rod moveable within the guide pin, and b) the blade at a distal end of the rod,
wherein the guide pin includes an internal passageway and an opening adjacent a distal end thereof, the blade projecting through the opening when in the deployed position,
wherein the blade is moveable between a folded position substantially parallel to the rod and a cutting position substantially normal to the rod,
wherein the rod includes a hinge distal of the blade when the blade is in the folded position; and
wherein the hinge biases the blade to the cutting position.

2. The cartilage trimmer as recited in claim 1, wherein the opening is at a distal end of the guide pin.

3. A method of using a cartilage trimmer, comprising:
moving a cutter distally within an internal passageway of a guide pin, wherein the cutter comprises a rod and a blade connected to a distal end of the rod, wherein the blade has a cutting surface only on a proximal edge of the blade, wherein during the moving step the blade is in a folded position and is substantially parallel to the rod, and wherein during the moving step a hinge of the rod is distal of the blade; and
deploying the blade from the folded position to a cutting position by passing the blade through an opening adjacent a distal end of the guide pin and under a bias of the hinge.

4. The method as recited in claim 3, further comprising:
resecting cartilage with the blade.

5. The method as recited in claim 4, wherein the cartilage is articular cartilage.

6. The method as recited in claim 4, further comprising:
adjusting an angle of the blade relative to the guide pin while resecting cartilage.

\* \* \* \* \*